United States Patent [19]
Vlock

[11] Patent Number: 5,165,914
[45] Date of Patent: Nov. 24, 1992

[54] ORAL COMPOSITIONS CONTAINING ZINC LACTATE COMPLEXES

[75] Inventor: Richard S. Vlock, Gloversville, N.Y.

[73] Assignees: David G. Vlock, N.Y.; Lawrence Rosen, Calif.

[21] Appl. No.: 780,915

[22] Filed: Oct. 22, 1991

Related U.S. Application Data

[63] Continuation-in-part of Ser. No. 663,511, Mar. 4, 1991, Pat. No. 5,094,845.

[51] Int. Cl.$^5$ .................. A61K 7/18; A61K 33/16; A61K 33/30
[52] U.S. Cl. ............................... 424/52; 424/49; 424/641; 424/642; 424/643; 424/673; 424/676
[58] Field of Search .................. 424/49, 52, 673, 676, 424/641, 642, 643

[56] References Cited

U.S. PATENT DOCUMENTS

| | | | |
|---|---|---|---|
| 4,289,754 | 9/1981 | Dhabhar et al. | 424/52 |
| 4,325,939 | 4/1982 | Shah | 424/55 |
| 4,469,674 | 9/1984 | Shah et al. | 424/52 |
| 4,749,561 | 6/1988 | Lane et al. | 424/52 |
| 4,749,562 | 6/1988 | Lane et al. | 424/52 |
| 4,863,722 | 9/1989 | Rosenthal | 424/52 |
| 4,937,066 | 6/1990 | Vlock | 424/52 |
| 5,094,845 | 3/1992 | Vlock | 424/52 |

*Primary Examiner*—Shep K. Rose
*Attorney, Agent, or Firm*—Ostrolenk, Faber, Gerb & Soffen

[57] ABSTRACT

Ammonium and alkali metal zinc lactate complexes used in oral compositions such as gingival and subgingival irrigating solutions, dentifrices, mouthwashes, and the like as well as in other preparations for treating oral lesions.

8 Claims, No Drawings

ORAL COMPOSITIONS CONTAINING ZINC LACTATE COMPLEXES

PRIOR APPLICATION

This application is a continuation-in-part of Ser. No. 663,511, filed Mar. 4, 1991, now U.S. Pat. No. 5,094,845.

The present invention relates to oral compositions containing a zinc metal complex, and more particularly, to oral compositions containing minor amounts of ammonium or alkali metal zinc lactate complexes, alone or in admixture with ammonium or alkali metal tartrate and/or gluconate complexes.

BACKGROUND OF THE INVENTION

As set forth in applicant's U.S. Pat. No. 4,937,066, it was previously recognized that zinc ions derived from zinc compounds employed in dentifrices, oral rinses, mouthwashes and the like have the beneficial effect of reduction of calculus formation and undesirable mouth odor. Zinc chloride has been used for many years, but it is very astringent and has an unpleasant taste that is difficult to mask. In a mouthwash or oral rinse formulation zinc chloride has a pH of about 3.0 which accounts for its high level of astringency.

Insoluble zinc salts such as zinc citrate and zinc carbonate have been used in dentifrice compositions (Pasternak U.S. Pat. No. 1,861,189 and Bley U.S. Pat. No. 1,943,467). Moreover, zinc citrate has been used for periodontal treatment and in dentifrices as a calculus and plaque control agent. Pader in U.S. Pat. No. 4,100,269 has claimed a long list of insoluble zinc compounds all of which do not provide a sufficient amount of zinc ions because of poor solubility.

In U.S. Pat. No. 4,289,755 (Dhabhar) insoluble zinc citrate is employed and solvated by means of an excess of citric acid in an attempt to overcome the relative insolubility problem of zinc compounds. U.S. Pat. No. 4,289,754, also issued to Dhabhar, employs sodium or ammonium zinc citrate as a novel soluble zinc compound, partially overcoming the problem of solubility discussed in U.S. Pat. No. 4,289,755. However, the solubility of sodium zinc citrate is given as only 1.17 g/100 ml, thus precluding a concentration of the zinc salt of more than about 1.2%. In U.S. Pat. No. 4,469,674 zinc salicylate is employed as a source of zinc ions. As set forth above, due to insolubility of the previously proposed zinc compounds it is impossible to formulate high concentrations of zinc ions. The sodium zinc citrate of U.S. Pat. No. 4,325,939 is stated to have a solubility of about 1.2%, which, while greater than that of zinc citrate, still falls short of providing a desirable concentration of zinc ions.

U.S. Pat. No. 4,937,066 overcomes the limitations noted above by utilizing the more soluble ammonium and alkali metal zinc tartrates.

BRIEF DESCRIPTION OF THE INVENTION

In accordance with the present invention, novel zinc derivatives such as ammonium or alkali metal zinc lactates have been prepared which are stable, freely soluble in water, have a neutral pH and a lower astringency than other zinc compounds. The ammonium or alkali metal zinc lactates are stable over a wide range of pH and are not precipitated or deactivated by fluoride ions, which is another problem recognized in the prior art. Moreover, these complexes are soluble to the extent of about 49 grams per 100 ml of water at pH 7 and thus can be prepared in aqueous solutions of up to 50% by weight, if desired. For some purposes it might be useful to prepare mixtures of ammonium or alkali metal zinc lactates with ammonium or alkali metal zinc tartrates or gluconates.

DETAILED DESCRIPTION OF THE INVENTION

An alkali metal zinc lactate $(M_2Zn(C_3H_5O_3)_2)$, wherein M is ammonium or an alkai metal, is prepared by admixing a suspension of zinc lactate in water with ammonium hydroxide or alkali metal hydroxide until the solution is clear and all of the zinc lactate is dissolved. The pH of the clear solution is 7.0 when ammonium or potassium hydroxide is used. The resulting solution can be used as is or evaporated to dryness to obtain the solid complex. The reaction may be carried out at ambient temperature in water, as set forth in the following example.

EXAMPLE 1

In a suitable reaction vessel, 1 gram of zinc lactate and 1 gram of zinc tartrate were suspended in 10 ml of water, and the suspension was stirred mechanically. Sufficient ammonium hydroxide was added to the mixture until a clear solution resulted which was then diluted with lactic acid (85%) to produce a solution of ammonium zinc lactate and ammonium zinc tartrate complexes. The solution had a pH of 7 and was odorless. When evaporated under gentle heat in a suitable vessel a solid zinc complex was obtained. The powdered material also was odorless and very soluble in water.

EXAMPLE 2

Ammonium zinc lactate was prepared by the procedure of Example 1 utilizing 2 grams of zinc lactate and 10 ml of water. The resulting solution was odorless.

EXAMPLE 3

Potassium zinc lactate-potassium zinc gluconate was prepared by the procedure of Example 1 utilizing 1 gram of zinc gluconate, 1 gram of zinc lactate, and 10 ml of water. Potassium hydroxide was substituted for the ammonium hydroxide.

EXAMPLE 4

A complex of potassium zinc lactate was prepared by suspending 1 gram of zinc lactate in 2 ml water. To this suspension was added 1 ml of lactic acid and sufficient concentrated potassium hydroxide to neutralize and clear the suspension.

The ammonium or alkali metal lactate complexes of the present invention have a number of important advantages over the ammonium and alkali metal complexes of U.S. Pat. No. 4,937,066. For one thing, the alkali metal zinc lactate complexes are more soluble in water than the tartrate complexes. Thus, for example, potassium zinc lactate has a solubility of 49.7 grams per 100 ml of water compared to the 31 grams solubility of potassium or ammonium zinc tartrate. Potassium zinc lactate, in contrast to potassium zinc tartrate is stable at a pH of 7. Moreover, ammonium or alkali metal zinc lactates are odorless and have little, if any, taste.

The invention is further illustrated by the following formulations:

| FORMULATION A - A Mouthwash and Oxygenating Rinse | |
| --- | --- |
| Water | 400 ml |
| Urea Peroxide | 40 gm |
| Potassium Zinc Lactatae | 10 gm |
| Sodium Lauryl Sulfate | 1.0 gm |
| Sodium Saccharin | 0.125 gm |
| Alcohol | 10 ml |
| Flavor | 5 ml |
| Color | q.s. |

| Component | Parts by Weight |
| --- | --- |
| FORMULATION B - A Toothpaste | |
| Glycerin | 10.00 |
| Sorbitol 70% in water | 10.00 |
| Dicalcium Phosphate | 30.00 |
| Sodium Lauryl Sulfate | 1.50 |
| Potassium Zinc Lactate | 5.00 |
| Sodium Fluoride | 2.00 |
| Magnesium Aluminum Silicate | 0.80 |
| Methyl Paraben[1] Preservative | 0.06 |
| Propyl Paraben[2] Preservative | 0.02 |
| Flavor | 1.00 |
| Distilled Water | Balance to 100.00 |
| FORMULATION C - An Antiplaque Dentifrice | |
| Glycerin | 15.00 |
| Sorbitol 70% in water | 5.00 |
| Dicalcium Phosphate | 30.00 |
| Sodium Monofluorophosphate | 2.00 |
| Sodium Lauryl Sulfate | 2.00 |
| Sodium Carboxymethyl Cellulose | 2.00 |
| Potassium Zinc Lactate | 2.00 |
| Potassium Zinc Tartrate | 1.00 |
| Triclosan[3] Bacteriostat | 0.20 |
| Flavor | 1.00 |
| Distilled Water | Balance to 100.00 |

[1] Methyl-p-hydroxybenzoate
[2] Propyl-p-hydroxybenzoate
[3] 5-Chloro-2-(2,4-dichlorophenoxy) phenol In the prior art formulations containing both zinc ions and fluoride ions were not practical; since, as discussed above, insoluble zinc fluoride was formed, thereby effectively eliminating both ions from the solution. In contrast, the novel ammonium and alkali metal zinc lactates of the present invention are compatible with fluoride ions over a wide range of concentrations without forming any insoluble precipitates. Thus, incorporating the protective action of fluoride and the antiplaque action of zinc in a single oral rinse or dentifrice formulation is entirely practical. For example, the preferred liquid dentifrices may be conveniently prepared by simple addition of ingredients, in no particular order, to a water or water/alcohol solvent system containing the aforementioned zinc complexes and fluoride compounds.

Optional ingredients include, for example, a humectant such as glycerine, sorbitol, polyethylene glycol, and the like to give a moist feel in the mouth, generally in amounts up to about 20.0 percent by weight, and preferably from about 5.0 to about 20.0 percent by weight. Additional additives include, but are not limited to, a nonionic antimicrobial agent such as Triclosan, generally from about 0.1 percent to 2.0 percent, preferably from about 0.2 percent to 0.5 percent; a natural or synthetic sweetening agent such as dextrose, levulose, mannitol, saccharin, cyclamate, and the like, generally from about 0.05 to about 2.0 percent by weight; a flavoring agent such as peppermint oil, spearmint oil, orange oil and the like, generally from about 0.01 to about 2.0 percent by weight; and a surface-active or sudsing agent such as, for example, a sodium alkyl benzene sulfonate, sodium alkyl sulfate or a nonionic or anionic organic synthetic detergent, generally from about 0.05 to about 10.0 percent by weight, preferably from about 0.5 to about 5.0 percent by weight.

All of the above are conventional surfactants utilized in dentifrice formulations. As set forth in U.S. Pat. No. 4,459,764 (Shah), when preparing substantially solid or semi-solid oral compositions such as dental creams, pastes and gels, the liquids and solids should be proportioned to form an extrudable creamy mass of desirable consistency. Liquids in these formulations will generally comprise chiefly water, glycerin, sorbitol, propylene glycol or the like, including suitable mixtures thereof.

It is usually advantageous to employ a mixture of both water and a humectant or binder such as glycerin or sorbitol, preferably glycerin. The total liquid content will generally be about 20 to 75 percent by weight of the formulation. It is also preferred to use a gelling agent such as a natural or synthetic gum and gumlike material, e.g. Irish Moss, gum traganacanth, xanthan gum, Veegum regular, sodium carboxymethylcellulose, polyvinylpyrrolidone, starch and the like. The Irish Moss and sodium carboxymethylcellulose are particularly compatible and are preferred gelling agents. The gum content is usually in an amount up to about 10 percent and preferably about 0.5 to 5 percent by weight of the formulation.

An essential ingredient in dental cream fornulations is an effective abrasive amount of a suitable dental abrasive, generally from about 10 to 60 percent by weight and preferably from about 20 to about 50 percent by weight. As noted previously, this abrasive must not interact with either the zine or fluoride component. Typical compatible abrasives include, for example, insoluble metaphosphates, finely divided silicas, bentonite and the like. The preferred abrasive is silica.

Various other materials may be incorporated as adjuvants in dental creams. Examples thereof are coloring or whitening agents, preservatives, silicones, chlorophyll compounds, ammoniated materials such as urea, diammoniumphosphate and mixtures thereof, and other constituents. A small amount of colloidal silica, for example, is often incorporated into toothpaste formulations as a thickener, giving some body to the formulation upon swelling when in contact with water. The foregoing adjuvants are suitably selected and incorporated in the instant compositions in amounts which do not have a substantially adverse effect on the properties an characteristics desired for the particular type of composition.

It will be further understood that the invention as described and illustrated above can be modified without departing from the basic concept, that is the use in oral compositions of ammonium or alkali metal zinc lactate as a source of zinc ions either in the presence of absence of fluoride ions. Thus, for example, sodium zinc lactate can be produced using sodium hydroxide in place of potassium hydroxide.

What is claimed is:

1. An oral composition comprising about 0.01 to 1% by weight of an anticaries and/or antiplaque-effective fluoride compound, about 0.1 to 15.0% by weight of an ammonium or alkali metal zinc lactate complex, and a carrier suitable for use in an oral cavity.

2. The oral composition of claim 1 wherein the fluoride compound is selected from the group consisting of sodium fluoride, potassium fluoride, stannous fluoride, and sodiummonofluorophosphate.

3. The oral composition of claim 1 containing a nonionic antimicrobial agent.

4. The oral composition of claim 1 wherein said zinc complex is ammonium zinc lactate.

5. The oral composition of claim 1 wherein the zinc complex is potassium zinc gluconate.

6. The oral composition of claim 1 wherein the zinc complex is an admixture of an ammonium or alkali metal zinc lactate and ammonium or alkali metal zinc tartrate.

7. The oral composition of claim 1 wherein the zinc complex is an admixture of an ammonium or alkali metal zinc lactate and ammonium or alkali metal zinc gluconate 8. The oral composition of claim 1 wherein the zinc complex is present in an amount from about 0.2% to about 10%.

* * * * *